United States Patent [19]

Matsumura et al.

[11] 4,435,397
[45] * Mar. 6, 1984

[54] CARBAMYLPIPERAZINE COMPOUNDS

[75] Inventors: Shingo Matsumura, Kyoto; Hiroshi Enomoto, Nagaokakyo; Yoshiaki Aoyagi, Kyoto; Haruo Tanaka, Hikone, all of Japan

[73] Assignee: Nippon Shinyaku Co., Ltd., Japan

[*] Notice: The portion of the term of this patent subsequent to May 26, 1998 has been disclaimed.

[21] Appl. No.: 247,881

[22] Filed: Mar. 26, 1981

[30] Foreign Application Priority Data

Apr. 8, 1980 [JP] Japan .................. 55-46443

[51] Int. Cl.³ .............. C07D 241/04; A61K 31/495; C07D 295/00
[52] U.S. Cl. .................. 424/250; 544/390; 544/391; 544/373; 544/376; 544/363; 544/366
[58] Field of Search ............. 544/390, 391; 424/250

[56] References Cited

U.S. PATENT DOCUMENTS

| | | | |
|---|---|---|---|
| 3,410,901 | 11/1968 | Kunz et al. | 260/501.17 |
| 3,410,910 | 11/1968 | Giordano et al. | 260/604 |
| 3,432,545 | 3/1969 | Howe | 260/501.17 |
| 3,637,852 | 1/1972 | Köppe et al. | 260/501.17 |
| 3,793,365 | 2/1974 | Winter et al. | 544/386 |
| 3,857,873 | 12/1974 | Schwender et al. | 260/501.17 |
| 3,872,147 | 3/1975 | Köppe et al. | 260/465 E |
| 3,935,267 | 1/1976 | Hauck et al. | 424/250 |
| 4,045,482 | 8/1977 | Murakami et al. | 260/501.18 |
| 4,269,838 | 5/1981 | Matsumura et al. | 544/390 |

FOREIGN PATENT DOCUMENTS

| | | | |
|---|---|---|---|
| 2942832 | 4/1980 | Fed. Rep. of Germany | 544/390 |
| 2439778 | 5/1980 | France | 544/390 |
| 55-57578 | 4/1980 | Japan | 544/390 |
| 701554 | 12/1953 | United Kingdom | 544/295 |
| 2052477 | 1/1981 | United Kingdom | 544/390 |

*Primary Examiner*—Donald G. Daus
*Assistant Examiner*—S. A. Gibson
*Attorney, Agent, or Firm*—Jacobs & Jacobs

[57] ABSTRACT

4-(3-Aryloxy-2-hydroxypropyl)piperazines bearing a carbamyl group in the 1-position are β-adrenergic blockers. A typical example is 1-carbamyl-4-{3-[2-allyl-3-(2-carbethoxyaminoethyl)phenoxy]-2-hydroxypropyl}piperazine.

8 Claims, No Drawings

CARBAMYLPIPERAZINE COMPOUNDS

DETAILED DESCRIPTION

This invention relates to 1-carbamylpiperazine derivatives substituted in the 4-position by a 3-aryloxy-propan-2-ol substituent.

It is well-known that the β-action of adrenalin is antagonized by various derivatives of phenoxypropanolamine and considerable study has been devoted to structure-activity correlations, particularly with regard to the organ selectivity arising from different substituents on the aromatic ring and different substituents on the amine. It has been considered essential for β-blockers of this type that the amine should be secondary; i.e., monosubstituted. Thus the amine substituent of known phenoxypropanol-type β-blockers almost without exception are secondary, isopropylamino and tert-butylamino being present in most of conventional structures. Tertiary amino structures appear to produce only very low activity. See, e.g., E. J. Ariëns, Ed.; Drug Design, Vol. III, p 205, Academic Press, New York 1972. See also, for example, U.S. Pat. Nos. 3,410,910, 3,432,545, 3,637,852, 3,872,147, 3,857,873, and 4,045,482. The compounds of this invention are piperazine derivatives and, therefore, analogous to tertiary-amino type. More significantly, these compounds have a carbamyl group in the 4-position of the piperazine ring. These structural features have never been seen in the prior compounds having β-adrenergic blocking activity. Surprisingly, compounds corresponding to the compounds of this invention but which lack the carbamyl group do not exhibit β-blocking activity at all. The blocking activity of the compounds according to this invention is extremely high, superior in fact to the activity of known β-blocker compounds.

The compounds according to this invention can be represented by the following structural formula:

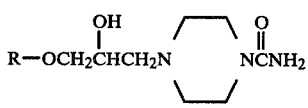 I or a pharmaceutically acceptable salt thereof, wherein R is

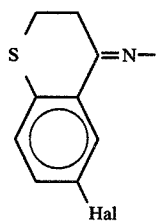 (a)

in which Hal is chloro, bromo, fluoro or iodo,

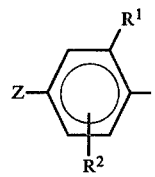 (b)

in which
R$^1$ is alkyl of up to 6 carbon atoms, cycloalkyl of 3 to 7 carbon atoms, alkanoyl of up to 6 carbon atoms or alkenyl of up to 6 carbon atoms,
R$^2$ is hydrogen or alkyl of up to 6 carbon atoms, and
Z is —CH$_2$CH$_2$NHCO$_2$R$^3$, —NHSO$_2$R$^3$ or

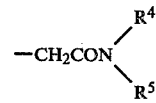

in which
R$^3$ is alkyl of up to 4 carbon atoms and each of R$^4$ and R$^5$ independently of the other is alkyl of up to 4 carbon atoms, or
(c) a bicyclic group of the formula

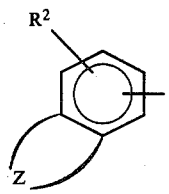

in which
Z is a chain of 3 or 4 atoms, said chain being selected from the group consisting of —(CH$_2$)$_2$(CH$_2$)$_n$—; —CH=CH—(CH$_2$)$_n$—;

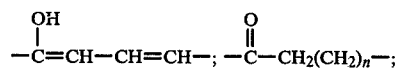

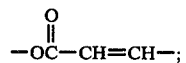

—NHCH=CH—; —NHCOCH$_2$CH$_2$—, and —N=C(SH)—NH—;
n has a value of 1 or 2 and
R$^2$ is as herein defined.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term halo denotes the monovalent substituents fluoro, chloro, bromo and iodo.

The compounds of the present invention can exist as optical isomers and both the racemates of these isomers and the individual isomers themselves are within the scope of the present invention. The racemates can be separated into their individual isomers through through the well-known technique such as forming diastereoisomeric salts.

The compounds of this invention interfer with the transmission of postganglionic impulses by blockage of the sympathetic receptor. Blockage of the β-receptor decreases inotropic, chronotropic and metabolic effects on the heart and in some cases can stop arrhythmias produced by excess epinephrine. Angina can in some instances be prevented as a result of the decreased need for oxygen by the heart.

β-Receptor blockers are characterized by their antagonism to isoproterenol (N-isopropyl-nor-adrenaline) and practical use of these compounds are those clinical conditions such as hypertension, angina, arrhythmia and the like where β-receptor blocking or isoproterenol antagonism is indicated.

In view of the nature of the indications, the dose administered must be carefully titrated to the patient, utilizing sound professional judgement and taking into consideration the age, weight and condition of the patient and the desired response. Generally a response will be observed for a patient of average weight (e.g., about 70 kg) at an oral dose of 5 to 50 mg 1 to 4 times a day, e.g., a daily dose of from 5 to 200 mg. A typical parenteral dose (i.v.) is from 1 to 5 mg for a patient of average weight slowly administered.

The compounds of the present invention are administered parenterally or orally in any of the usual pharmaceutical forms. These include solid and liquid oral unit dosage forms such as tablets, capsules, powders, suspensions, solutions, syrups and the like, including sustained released preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuiting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat or shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The toxicity of the compounds is favorable. Moreover, they have a high degree of specificity. Thus they tend to specifically control only spontaneous movement of heart, especially pulse, with relatively little effect on heart muscle contraction. This is one of the most characteristic pharmacological action of the carbamoylpiperazinopropanol compounds of the present invention and is in marked contrast with other known β-blockers, such as propanlol.

These properties can be conveniently observed in recognized animal models. Thus the inhibitory effect on spontaneous movement of the isolated rat auricle is measured at a concentration of $10^{-5}$ g/ml and then expressed (by application of the three point method) as a ratio to propanolol (=1.0). Representative data are given for compounds of formulas 1(a), 1(b), and 1(c).

TABLE 1(a)

| Compound No. | Hal. | Ratio of Pulse Inhibition | Ratio of Heart Muscle Concentration Inhibition |
|---|---|---|---|
| 2 | Br | 1.845 | 0.441 |
| Propanolol | — | 1.0 | 1.0 |

TABLE 1(b)

| Cmpd. No. | $R^1$ (2-) | $R^2$ (Position) | Z (4-) | Ratio of Pulse Inhibition | Ratio of Heart Muscle Con. Inhibition |
|---|---|---|---|---|---|
| 1 | —CH$_3$ | —CH$_3$ (3) | —SO$_2$CH$_3$ | 0.711 | 0.154 |
| 7 | —CH$_3$ | H | —CH$_2$CH$_2$NHCO$_2$CH$_3$ | 0.733 | −0.038 |
| 18 | —CH$_2$CH=CH$_2$ | H | —CH$_2$CH$_2$NHCO$_2$C$_2$H$_5$ | 1.002 | 0.013 |
| 19 | —CH$_2$CH=CH$_2$ | H | —CH$_2$CON(C$_2$H$_5$)$_2$ | 0.821 | 0.150 |
| 20 | —CH(CH$_3$)$_2$ | H | —CH$_2$CH$_2$NHCO$_2$CH$_2$CH(CH$_3$)$_2$ | 0.983 | 0.050 |

TABLE 1(b)-continued

| Cmpd. No. | R¹ (2-) | R² (Position) | Z (4-) | Ratio of Pulse Inhibition | Ratio of Heart Muscle Con. Inhibition |
|---|---|---|---|---|---|
| 21 | —CH(CH$_3$)$_2$ | —CH$_3$ (5) | —CH$_2$CON(C$_4$H$_9$)$_2$ | 0.881 | 0.134 |
| 22 | —C(CH$_3$)$_3$ | H | —CH$_2$CH$_2$NHCO$_2$C$_2$H$_5$ | 1.022 | −0.151 |
| 23 | cyclohexyl | H | —CH$_2$CONHC$_4$H$_9$ | 1.190 | 0.157 |
| 24 | —CH(CH$_3$)$_2$ | H | —NHSO$_2$C$_3$H$_7$ | 1.157 | 0.168 |
| propranolol | — | — | — | 1.0 | 1.0 |

TABLE 1(c)

| Compd. No. | R | Ratio of Pulse Inhibition | Ratio of Heart Muscle Con. Inhibition |
|---|---|---|---|
| 6 | 1,2,3,4-tetrahydronaphth-8-yl | 0.696 | 0.333 |
| 3 | 4-oxo-1,2,3,4-tetrahydronaphth-8-yl | 0.459 | 0.154 |
| 4 | 5-hydroxynaphth-1-yl | 0.487 | 0.165 |
| 9 | 1,2-dihydronaphth-8-yl | 1.002 | 0.239 |
| 8 | inden-7-yl | 0.821 | 0.282 |
| 5 | 2-oxo-5-methylchromen-8-yl | 0.629 | 0.408 |
| propanolol | — | 1.0 | 1.0 |

The compounds can be prepared by a number of methods previously utilized for other compounds of this type. The most general route comprises preparation of N-carbamylpiperazine and allowing the same to react with a glycidyl ether bearing the group designated as R. Alternatively an appropriately substituted glycidyl ether is allowed to react with piperazine and N-carbamylation is then effected on the reaction product. The carbamylation reaction is conducted conventionally with a cyanate or nitrourea. For N-alkylcarbamylation, a reactive carbamylating agent such as N-alkylcarbamyl chloride or an alkyl isocyanate can be employed with advantage.

The synthesis of some representative compounds is described in the following examples.

EXAMPLE 1

Synthesis of compound (1) R=

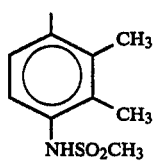

2,3-Dimethyl-4-aminophenol (5.7 g) [cf. Compt. rend., 259, 4719 (1964)] is dissolved in 50 ml. of pyridine, 9.6 g of methanesulfonyl chloride is dropped thereinto with cooling, the mixture is stirred for three hours, and kept overnight at room temperature. The reaction mixture is poured over ice, the separated crystals are collected by filtration, and recrystallized from ethyl acetate. M.p. 148°–150° C. Yield 6.5 g.

The resulting 2,3-dimethyl-4-methanesulfonaminophenol (4.0 g) is heated at reflux for four hours with 6.0 g of potassium carbonate (anhydrous) and 25 g of epibromohydrin in 100 ml. of methyl ethyl ketone. After the reaction, insoluble matters are removed by filtration, the solvent is evaporated to dryness in vacuo, and the residue is purified by silica gel column chromatography with 2:1 benzene:ethyl acetate. Colorless and oily reaction product is obtained in 4.1 g yield.

The resulting epoxy compound (4.0 g) and 2.0 g of N-carbamoylpiperazine are heated to reflux for six hours in 100 ml of methanol. After the reaction, the reaction solution is evaporated to dryness in vacuo and the resulting residue is purified by silica gel column chromatography 8:1 to 3:1 chloroform:methanol. The purified product is recrystallized from ether. Melting point: 113°–115° C. Yield 4.8 g.

EXAMPLE 2

Synthesis of compound (2) R=

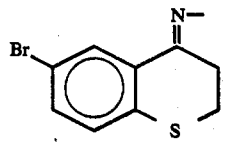

Oxime sodium salt prepared from 6-bromothiochroman-4-one oxime and sodium methoxide is heated to reflux in toluene with epichlorohydrin. The resulting 3-(6-bromothiochroman-4-ylideneoximide)-1,2-epoxypropane (2.0 g) [cf. Europ. J. Med. Chem. 13, 347 (1978)] is heated to reflux with N-carbamoylpiperazine in 40 ml of ethanol for six hours. After the reaction, the reaction mixture is evaporated to dryness in vacuo and the residue obtained is purified by silica gel column chromatography. (Solvent: a 5:1 mixture of chloroform and methanol). Colorless crystals are obtained in 2.6 g yield. Melting point: 101°–102° C. Hydrochloride recrystallized from ethanol melts at 186°–188° C.

The same procedures as above are carried out starting with 6-fluorothiochroman-4-one oxime to yield 1-carbamyl-4-[3-(6-fluorothiochroman-4-ylideneoximide)-2-hydroxypropyl]piperazine, the hydrochloride of which, after recrystallization from ethanol, melts at 185°–187° C.

EXAMPLE 3

Synthesis of compound (3) R=

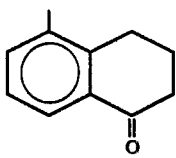

3 13 grams of α-tetralon-5-yl glycidyl ether [J. Pharm. Sci. 60, 1589 (1971)] prepared from 5-hydroxy-α-tetralone and epichloro hydrin is heated to reflux for six hours in 40 ml of methanol with 1.95 g of N-carbamoylpiperazine. After the reaction, the reaction solution is evaporated to dryness in vacuo and the resulting residue crystals are recrystallized from ethanol ether mixture. Melting point 178°-179° C. Yield 3.9 g. Hydrochloride recrystallized from ethanol melts at 149°-153° C.

EXAMPLE 4

Synthesis of compound (10) R =

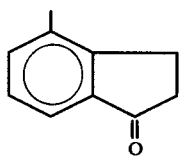

3,4-Dihydrocumarine is allowed to react with anhydrous aluminum chloride at 200° C. and the resulting 4-hydroxyindanone is allowed to react with epichlorohydrin in an aqueous solution of sodium hydroxide to give 4-(2,3-epoxypropoxy)-1-indanone (cf. Japanese Patent No. Sho-48-817).

The resulting indanone glycidyl ether (6.15 g) is heated to reflux for three hours and a half in 90 ml of methanol with 3.87 g of N-carbamoylpiperazine. After the reaction, the reaction solution is evaporated to dryness in vacuo and the residual crystals are recrystallized from a mixture of ethanol and n-hexane. Melting point of the product: 161°-163° C. Yield 6.98 g. Hydrochloride recrystallized from ethanol melts at 143°-150° C.

EXAMPLE 5

Synthesis of compound (8) R =

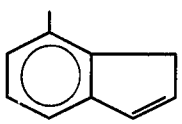

4-Hydroxy-1-indene is prepared starting from 4-hydroxyindanone via 1,4-indanediol, 4-acetoxy-1-indanol and 4-acetoxy-1-indene in this order. The resulting 4-hydroxy-1-indene is allowed to react with epichlorohydrin in an aqueous solution of sodium hydroxide to give 4-(2,3-epoxypropoxy)indene. [cf. Yakugaku Zasshi 92, 1358 (1972)].

The resulting indene glycidyl ether (1.80 g) is heated to reflux for four hours in 50 ml of methanol with 1.24 g of N-carbamoylpiperazine. After the reaction, methanol is evaporated therefrom and the residual crystals are recrystallized from a mixture of ethanol and ethyl acetate. Melting point of the product: 217°-129° C. Yield .84 g. Hydrochloride recrystallized from ethanol melts at 185°-190° C.

EXAMPLE 6

Synthesis of compound (9) R =

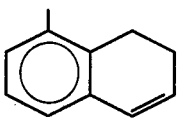

7,8-Dihydro-α-naphthol prepared from 5-hydroxy-α-tetralone is allowed to react with epichlorohydrin in an aqueous solution of sodium hydroxide to give 1-(2,3-epoxypropoxy)-7,8-dihydronaphthalene [cf. J. Med. Chem. 21, 913 (1978)].

The resulting epoxy compound (1.49 g) is heated to reflux for five hours with 0.97 g of N-carbamoylpiperazine in 40 ml of methanol. After the reaction, methanol is evaporated from the reaction mixture in vacuo and the residual crystals are recrystallized from ethanol to give 1.94 g of the product. Melting point: 163°-164° C. Hydrochloride recrystallized from ethanol melts at 201°-203° C.

EXAMPLE 7

Synthesis of compound (4) R =

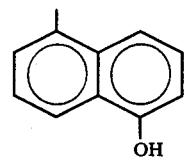

1,5-Dihydroxynaphthalene is allowed to react with equimolar sodium ethoxide in ethanol to give the corresponding sodium salt which is further allowed to react with epichlorohydrin to give 1-(2,3-epoxypropoxy)-5-hydroxy naphthalene.

2.73 grams of the above product are heated at reflux for five hours in 70 ml of methanol with 1.63 g of N-carbamoylpiperazine. After the reaction, methanol is evaporated in vacuo therefrom, and the residue is purified by silica gel column chromatography utilizing 5:1 chloroform:methanol. The purified product is recrystallized from ethanol to give 3.2 grams of the product. Melting point 93°-94° C. Hydrochloride recrystallized from ethanol melts at 149°-151° C.

EXAMPLE 8

Synthesis of compound (6) R =

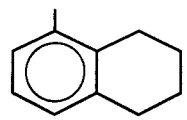

5,6,7,8-Tetrahydro-1-naphthol is allowed to react with sodium methoxide in methanol to give the corresponding sodium salt which is further allowed to react with epichlorohydrin to give 1-(2,3-epoxypropoxy)-5,6,7,8-tetrahydronaphthalene (cf. Japanese Pat. No. Sho-52-53842).

The resulting epoxy compound (10 g) and 7 g of N-carbamoylpiperazine are heated at reflux for 2.5 hours in 140 ml of methanol. After the reaction, methanol is removed therefrom in vacuo and the residual crystals are recrystallized from a mixture of ethanol and n-hexane to give 10.74 g of the product, melting point 134°-136° C. Hydrochloride recrystallized from ethanol melts at 189°-193° C.

EXAMPLE 9

Synthesis of compound (5) R =

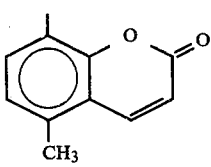

5-Methyl-8-hydroxycumarin (synthesized from isovanilin in 4 steps) is allowed to react with epibromohydrin in methyl ethyl ketone in the presence of potassium carbonate to give 5-methyl-8-(2,3-epoxypropoxy)-cumarin [cf. Chem. Phar. Bull. 20,205 (1972)].

The resulting epoxy compound (3.0 g) is heated at reflux for seven hours with 1.75 g of N-carbamoylpiperazine in 50 ml of methanol. After the reaction, methanol is evaporated therefrom in vacuo and the residue is purified by silica gel column chromatography with (3:1) chloroform:methanol. The purified product is recrystallized from ether to give 3.2 g of the product, melting point: 171°-173° C.

EXAMPLE 10

Synthesis of compound (11) R=

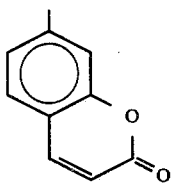

Five grams of 7-(2,3-epoxypropoxy)cumarin obtained by the reaction of 7-hydroxycumarin with epibromohydrin in methyl ethyl ketone in the presence of anhydrous potassium carbonate is heated at reflux for seven hours with 3.1 g of N-carbamoylpiperazine in 100 ml of methanol. After the reaction, methanol is evaporated therefrom in vacuo and the residual crystals are washed with ethyl acetate to give 7.9 g of the product. Hydrochloride recrystallized from a mixture of ethanol and dimethyl formamide melts at 198°-200° C.

EXAMPLE (11)

Synthesis of compound (12) R=

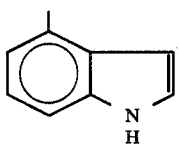

4-Hydroxy indole is allowed to react with epichlorohydrin to give 4-(2,3-epoxypropoxy)indole, (cf. Netherlands Pat. No. 6,601,040).

This compound (1.92 g) is heated at reflux for six hours in 60 ml of methanol with 1.38 g of N-carbamoylpiperazine. After the reaction, methanol is evaporated therefrom in vacuo and the residual crystals are recrystallized from methanol to give 2.6 g of the product. Melting point: 193°-195° C. Hydrochloride recrystallized from ethanol melts at 184°-187° C.

EXAMPLE 12

Synthesis of compound (13) R=

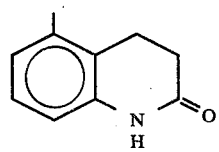

5-Hydroxy-3,4-dihydro-2-quinoline (prepared in three steps from cyclohexane-1,3-dione and acrylonitrile) is allowed to react with epichlorohydrin to give 5-(2,3-epoxypropoxy)-3,4-dihydro-2-quinolinone [J. Med. Chem. 17,529 (1974)].

The product (0.4 g) is heated at reflux for three hours in 20 ml of methanol with 0.27 g of N-carbamoylpiperazine. After the reaction, methanol is evaporated therefrom in vacuo and the residual product is purified by silica gel column chromatography (solvent: an 8:1 mixture of chloroform, and methanol). The purified product is recrystallized from a mixture of ethanol and n-hexane to give 0.50 g of the product. Melting point: 200°-203° C.

EXAMPLE 13

Synthesis of the compound (14) R=

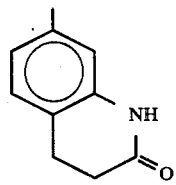

m-Hydroxyaniline is allowed to react with β-chloropropionyl chloride and in two steps, 7-hydroxy-3,4-dihydro-2-quinolinone is obtained. This is allowed to react with epichlorohydrin to give 7-(2,3-epoxypropoxy)-3,4-dihydro-2-quinolinone.

The resulting epoxy compound (1.0 g) is heated to reflux for two hours and a half in 30 ml of methanol with 0.6 g of N-carbamoylpiperazine. After the reaction, methanol is evaporated therefrom in vacuo and the residual product is purified by silica gel column chromatography (with 8:1 chloroform:methanol). The purified product is recrystallized from a mixture of ethanol and n-hexane to give 0.93 g of the product melting point 85°-90° C. Hydrochloride recrystallized from ethanol melts at 154°-157° C.

EXAMPLE 14

Synthesis of compound (15) R=

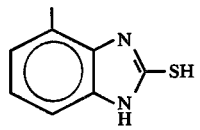

N-Carbamoylpiperazine (1.11 g) is heated to reflux for six hours in 20 ml of methanol with 2-(2,3-epoxypropoxy)-4-methyl-6-nitroaniline (1.83 g) prepared in six steps from m-cresol. After the reaction, methanol is evaporated therefrom in vacuo and the residual product is purified by silica gel column chromatography with 4:1 chloroform:methanol to give 2.1 g of a reddish orange colored glass-like substance. Mass spectrum: M+ m/e=353, base peak m/e=99.

The resulting reaction product (1.80 g) is dissolved in 50 ml of methanol. About 1 ml of Raney Nickel catalyst is added to the solution and the mixture is subjected to a catalytic reduction at ordinary temperature and pressure. After absorption of hydrogen gas thereinto ceases, the catalyst is removed by filtration and the filtrate is evaporated to dryness in vacuo. The resulting residue is dissolved in 30 ml of ethanol, 0.82 g of potassium xanthogenate is added to the solution, and the mixture is heated to reflux for six hours. After the reaction, ethanol is evaporated therefrom in vacuo and the residual product is purified by silica gel column chromatography (solvent: a 4:1 mixture of chloroform and methanol). The purified product is further recrystallized from ethanol to give 1.2 g of the product, melting point: 226°–229° C.

EXAMPLE 15

Synthesis of compound (16) R=

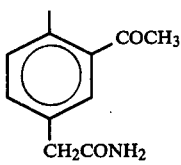

3-Acetyl-4-hydroxybenzyl cyanide (7.5 g) [cf. Yakugaku Zasshi 78, 647 (1957)] is warmed at 50° C. for two hours in 30 ml of concentrated hydrochloric acid. After being cooled, the mixture is poured over onto ice and the separated crystals are collected by filtration. The crystals are recrystallized from ethyl acetate to give 5.4 g of the intermediate, m.p. 162°–163° C.

This intermediate (3-acetyl-4-hydroxyphenylacetamide) (1.0 g) is dissolved in 10 ml of methanol in which 0.12 g of metal sodium is already dissolved, then 10 ml of epichlorohydrin is added thereto, and the mixture is heated to reflux for six hours with stirring. After the reaction, the reaction solution is evaporated to dryness, the resulting residual product is extracted with ethyl acetate, the extract layer washed with water, then dried, and evaporated to dryness in vacuo. The resulting residue (crystals) is recrystallized from ethyl acetate to give 0.75 g of the intermediate, melting point 85°–87° C.

The resulting intermediate, 3-acetyl-4-(2,3-epoxy-propxy)phenylacetamide (0.62 g), is heated to reflux for eight hours in 10 ml of methanol with 0.34 g of N-carbamoylpiperazine. After the reaction, methanol is evaporated therefrom in vacuo, and the residual reaction product is purified by silica gel column chromatography (3:1 chloroform:methanol) to yield 1.2 g of 1-carbamyl-4-[3-(2-acetyl-4-carbamylmethylphenoxy)-2-hydroxypropyl]piperazine as a colorless liquid. m.p. HCl 143°–145° C. (ethanol).

EXAMPLE 16

Synthesis of compound (7) R=

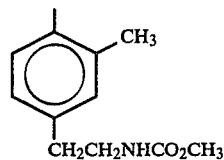

3-Methyl-4-methoxy benzaldehyde is heated to reflux for three hours in glacial acetic acid nitromethane in the presence of ammonium acetate and the resulting 3-methyl-4-methoxy β-nitrostyrene is reduced with zinc amalgum and hydrochloric acid in ethanol to give 3-methyl-4-methoxy β-phenethylamine. The resulting phenethylamine is heated to reflux for three hours in concentrated hydrobromic acid and, after the reaction, the reaction solution is evaporated to dryness in vacuo to give 3-methyl-4-hydroxy-β-phenethylamine hydrobromide as a residue.

The resulting hydrobromide is dissolved in 3% sodium hydroxide solution, methyl chlorocarbonate is added thereto, and the mixture is vigorously stirred for one hour at room temperature. When the reaction is completed, ammonium chloride is added to the reaction solution so that the solution is made ammonia-alkaline. Then the mixture is extracted with ethyl acetate to give colorless and oily N-carbomethoxy-3-methyl-4-hydroxy phenethylamine. NMR spectrum (in CDCl₃): 2.20 ppm; 3H singlet: 2.5–2.8 ppm, 2H triplet: 3.2–3.45 ppm, 2H triplet: 3.62 ppm, 3H singlet: 6.7–6.9 ppm, 3H multiplet.

Metal sodium (0.94 g) is dissolved in 40 ml of methanol, 8.58 g of the product obtained hereinabove is added thereto, the mixture is heated to reflux for six hours with 30 ml of epichlorohydrin and, after the reaction, the reaction solution is evaporated to dryness in vacuo. The resulting residue is extracted with ethyl acetate and the extract is purified by silica gel column chromatography in 2:1 benzene:ethyl acetate. Melting point: 56°–57° C. Yield 8.3 g.

The resulting N-carbomethoxy-3-methyl-4-(2,3-epoxypropoxy)-β-phenethylamine (4.0 g) is heated to reflux for six hours in 50 ml of methanol with 2.0 g of N-carbamoylpiperazine. After the reaction, methanol is evaporated therefrom in vacuo and chromatographed on silica gel with 4:1 chloroform:methanol to yield 5.8 g of 1-carbamyl-4-{3-[2-methyl-4-(2-carbomethoxyaminoethyl)phenoxy]-2-hydroxypropyl}piperazine as a colorless oil, m.p. HCl 174°–176° C. (ethanol).

EXAMPLE 17

Synthesis of compound (25) R=

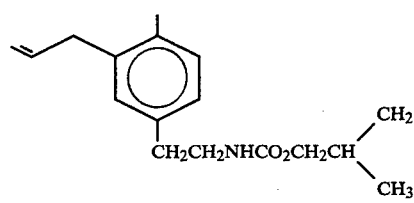

Tyramine hydrochloride (6.9 g) is dissolved in 50 ml of 10% aqueous solution of sodium hydroxide and 7.0 g of isobutyl chlorocarbonate is dropped thereinto with stirring. The mixture is stirred for thirty minutes at room temperature and then the reaction solution is made acidic with hydrochloric acid and extracted with ether. The extract is dissolved in 30 ml of isopropanol, 30 ml of 10% aqueous solution of sodium hydroxide is added thereto, and the mixture is stirred for thirty minutes at room temperature. The reaction solution is diluted with 200 ml of water, washed with ether, then made acidic with hydrochloric acid, and extracted with ether. A colorless, oily reaction product is obtained in 8.8 g yield.

This product (8.6 g) is dissolved in 100 ml of dimethylformamide, 6.6 g of allyl bromide and 7.0 g of anhydrous potassium carbonate are added thereto, and the mixture is heated at 70°-80° C. with stirring for three hours. The reaction solution is diluted with 400 ml of water and extracted with ether to give 6.4 g of N-carboisobutoxy-O-allyltyramine as pale yellow crystals with melting point 57°-59° C.

This compound (6.0 g) is heated at reflux in 25 ml of N,N-dimethylaniline for six hours. After being cooled, the reaction solution is diluted with ether, washed with 5% hydrochloric acid, and extracted with 2% aqueous solution of sodium hydroxide. This alkaline extract is immediately acidified with hydrochloric acid and extracted with ether to give 4.3 g of N-carboisobutoxy-3-allyltyramine. Melting point: 70°-71° C.

The resulting compound (4.0 g) is dissolved in 30 ml of dimethyl formamide, 10 ml of epibromohydrin and 5.0 g of anhydrous potassium carbonate are added thereto, and the mixture is heated at 70°-80° C. for three hours. The reaction solution is diluted with 200 ml of water and extracted with ether to give 5.0 g of colorless and oily reaction product. This is dissolved in 50 ml of methanol, 2.5 g of N-carbamoylpiperazine is added thereto, and the mixture is heated to reflux for two hours. The reaction solution is evaporated to dryness in vacuo and the residual product is purified by subjecting to silica gel column chromatography (solvent: a 10:1 mixture of chloroform and methanol). The resulting product, compound (25), is converted to its hydrochloride and is recrystallized from isopropanol to give 3.88 g of the product, melting point: 175°-178° C.

When ethyl chlorocarbonate is used instead of isobutyl chlorocarbonate and the same reaction as above is carried out, 1-carbamyl-4-{3-[2-allyl-4-(2-carbethoxyaminethyl)phenoxy]-2-hydroxypropyl}piperazine, compound 18, is obtained. Its hydrochloride, recrystallized from ethanol, melts at 165°-167° C.

EXAMPLE 18

Synthesis of compound (31) R=

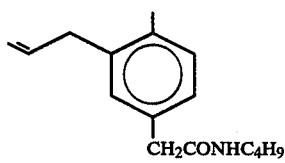

CH₂CONHC₄H₉ p-Hydroxyphenylacetic acid (5.0 g) is dissolved in 30 ml of dimethyl formamide, 10 ml of allyl bromide and 10 g of anhydrous potassium carbonate are added thereto, and the mixture is heated at 70°-80° C. for six hours with stirring. The reaction solution is diluted with 300 ml of water, extracted with ether, the resulting extract is dissolved in 100 ml of methanol, and the mixture is heated to reflux for one hour with 30 ml of 15% aqueous solution of potassium carbonate. The reaction solution is then concentrated in vacuo, 100 ml of water is added thereto, the mixture is washed with ether, acidified with hydrochloric acid, and extracted with ether to give 5.0 g of p-allyloxyphenylacetic acid, melting point: 61°-62° C.

This is dissolved with 50 ml of benzene, 4 ml of thionyl chloride is added thereto, and the mixture is heated to reflux for one hour. The reaction solution is evaporated to dryness in vacuo, the residual product is dissolved in 50 ml of benzene, 10 ml of n-butylamine is dropped thereinto with ice-cooling and stirring, and the reaction mixture is stirred for two hours at room temperature. The reaction solution is washed with 1% hydrochloric acid and evaporated to dryness to give 5.87 g of N-n-butyl-p-allyloxyphenylacetamide. Melting point 87°-89° C.

This is dissolved into 20 ml of N,N-dimethylaniline and the solution is heated to reflux for six hours. The reaction is cooled, diluted with 100 ml of ether, washed with 5% hydrochloric acid, extracted with 2% sodium hydroxide solution, the alkaline extract is immediately acidified with hydrochloric acid, and extracted with ether to give 4.8 g of N-n-butyl-3-allyl-4-hydroxyphenylacetamide. Melting point 48°-50° C.

The resulting compound (4.8 g) is dissolved in 30 ml of dimethyl formamide, 15 ml epibromohydrin and 10 g of anhydrous potassium carbonate are added thereto, and the mixture is heated at 75°-80° C. for two hours with stirring. The reaction mixture is diluted with 100 ml of water, extracted with ether, and the resulting extract is purified by subjecting to silica gel column chromatography (solvent: and 8:1 mixture of chloroform and ethyl acetate). The resulting oily phenyl glycidyl ether (4.3 g) is dissolved in 50 ml of methanol, 2.0 g of N-carbamoylpiperazine is added thereto, and the mixture is heated to reflux for two hours. The reaction mixture is evaporated to dryness in vacuo and the residual product is purified by subjecting to silica gel column chromatography to give the compound (31). (Solvent: a 10:1 mixture of chloroform and methanol). Hydrochloride recrystallized from isopropanol melts at 162°-164° C. Yield 5.18 g.

The similar reaction is carried out by the use of diethylamine instead of n-butylamine in the above reaction to yield 1-carbamyl-4-[3-(2-allyl-4-N,N-diethylcarbamylmethylphenoxy)-2-hydroxypropyl]piperazine, compound (19). The hydrochloride recrystallized from isopropanol melts at 126°-128° C. Yield 4.80 g.

EXAMPLE 19

Synthesis of compound (20) R=

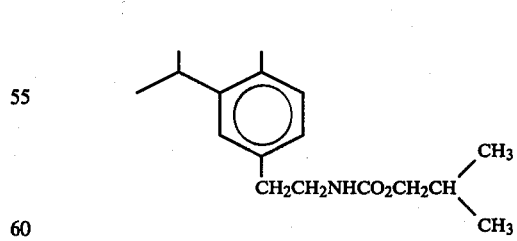

CH₂CH₂NHCO₂CH₂CH(CH₃)(CH₃)

Hydrochloric acid gas is bubbed into a mixture of 55 g of o-isopropylanisole, 35 g of formaline and 9 g of zinc chloride with ice cooling and stirring for hours. The reaction mixture is added to ice water and the mixture is extracted with ether to give 70 g of crude 3-isopropyl-4-methoxybenzyl chloride. Potassium cyanide (26 g) is added to 400 ml of acetonitrile, 100 mg of 18-crown 6 is added thereto, and the benzyl chloride compound obtained above is dropped thereinto with refluxing and stirring. After the dropping is completed, the mixture is heated to reflux for ten hours with stirring. The reaction solution is then concentrated in vacuo, water is added to the concentrate, and the mixture is extracted with ether. The resulting extract is purified by subjecting to a distillation in vacuo to give 40 g of 3-isopropyl-4-methoxybenzyl cyanide, boiling point under 1 mm Hg 120°–125° C.

Lithium aluminum hydride (2.4 g) is suspended in 100 ml of anhydrous ether, a solution of 8.2 g of anhydrous aluminum chloride in 50 ml of anhydrous ether is added thereto with stirring at room temperature, the mixture is stirred for five minutes, a solution of the above-obtained benzyl cyanide compound (10.6 g) dissolved in 20 ml of anhydrous ether is dropped into the reaction solution and the mixture is stirred for one hour. The reaction solution is then treated by the usual manner and the resulting basic substance is extracted with ether to give 8.6 g of colorless and oily 3-isopropyl-4-methoxy-$\beta$-phenethylamine.

The resulting phenethylamine compound (3.8 g) is dissolved in 50 ml of acetone, 8.2 g of anhydrous potassium carbonate is added thereto, 3.0 g of isobutyl chlorocarbonate is dropped thereinto with refluxing and stirring, and the mixture is heated to reflux for two hours. The reaction product is collected by filtration removing the insoluble matter, the filtrate obtained is evaporated to dryness in vacuo, 5.9 g of pale yellow and oily N-carboisobutoxy compound.

To 5 ml of ethyl mercaptan is added 13 g of anhydrous aluminum chloride with ice cooling, a solution of 4.7 g of the above N-carboisobutoxy compound dissolved in 5 ml of methylene chloride is added thereto, the mixture is stirred for five hours at room temperature, the reaction solution is poured over into ice, and extracted with ether to give 3.67 g of N-carboisobutoxy-3-isopropyl-4-hydroxy-$\beta$-phenethylamine. Melting point 87° C.

The resulting intermediate compound (4.9 g) is dissolved in 100 ml of dimethyl formamide, 4.16 g of anhydrous potassium carbonate and 4.11 g of epibromohydrin are added thereto, and the mixture is heated at 80° C. for five hours with stirring. The reaction solution is diluted with 400 ml of water and extracted with ethyl acetate. The extract is subjected to silica gel column chromatography (solvent: a 4:1 mixture of benzene and ethyl acetate) for purification and 4.16 g of oily reaction product is obtained.

This compound (3.88 g) is dissolved in 100 ml of methanol, 1.64 g of carbamoylpiperazine is added thereto, and the mixture is heated to reflux for five hours. The reaction solution is evaporated to dryness in vacuo and the residual product is purified by subjecting to silica gel column chromatography 5:11 chloroform:methanol to give the compound (20). Hydrochloride recrystallized from ethanol melts at 156°–158° C. Yield 4.2 g.

When ethyl chlorocarbonate is used instead of isobutyl chlorocarbonate in this procedure, there is obtained 1-carbamyl-4-{3-[2-isopropyl-4-(2-carbethoxyaminoethyl)phenoxy]-2-hydroxypropyl}-piperazine, compound (26). The hydrochloride, recrystallized from ethanol, melts at 153°–154° C.

EXAMPLE 20

Synthesis of compound (32) R=

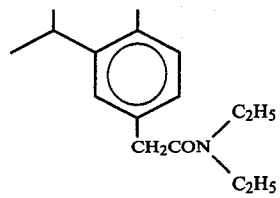

Ten grams of 3-isopropyl-4-methoxybenzyl cyanide obtained in Example 19 is dissolved in 25 ml of concentrated hydrochloric acid, the mixture is allowed to stand overnight at room temperature, then 70 ml of water is added thereto. The mixture is heated at 80° C. for six hours, cooled and extracted with ether. The extract is in turn extracted with 2% sodium hydroxide, the alkaline extract is then acidified with hydrochloric acid, and extracted with ether to give 8.2 g of 3-isopropyl-4-methoxyphenylacetic acid, melting point 94°–96° C.

The resulting phenylacetic acid compound (4.0 g) is heated at reflux for two hours with 5 ml of thionyl chloride. The reaction mixture is evaporated to dryness in vacuo, the residual product is dissolved in 15 ml of chloroform, the solution is dropped into an ice cooled mixture of 2.8 g of diethylamine and 30 ml of chloroform with stirring. The mixture is let stand for two hours at room temperature, washed with water, and evaporated to dryness to give 4.8 g of oily N,N-diethyl-3-isopropyl-4-methoxyphenylacetamide.

The resulting compound (4.7 g) is subjected to dimethylation reaction by the ethylmercaptan/aluminum chloride (Example 19) and 2.6 g of N,N-diethyl-3-isopropyl-4-hydroxyphenyl-acetamide is obtained. Melting point 112°–113° C.

The resulting 2.44 of hydroxyphenyl-acetamide compound is heated to reflux for three hours in 30 ml of dimethylformamide at 80° C. with 0.73 g of anhydrous potassium carbonate and 3.5 g of epibromohydrin, the reaction solution is diluted with 200 ml of water, extracted with ether, the resulting extract is immediately dissolved in 30 ml of methanol, 2.5 g of carbamoylpiperazine is added thereto, and the mixture is heated to reflux for six hours. The reaction solution is evaporated to dryness in vacuo and the residual product is purified by subjecting to silica gel column chromatography with 7:1 chloroform:methanol to give 1.4 g of the compound (32). Hydrochloride recrystallized from ethanol melts at 101°–110° C., yield 0.95 g.

The same reaction as above is carried out using dibutylamine instead of diethylamine to yield 1-carbamyl-4-[3-(2-isopropyl-4-N,N-diethylcarbamylmethylphenoxy)-2-hydroxypropyl]piperazine, compound (33). The hydrochloride, recrystallized from ethanol, melts at 102°–105° C.

EXAMPLE 21

Synthesis of compound (27) R=

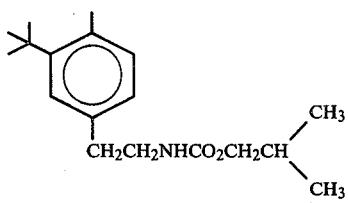

3-tert-Butyl-4-methoxybenzyl cyanide is obtained from o-t-butylanisole as in Example 19. This material (b.p. 140°–145° C./0.9 mmHg) is reduced with aluminum hydride as in Example 19 and the resulting phenethylamine compound is allowed to react with isobutyl chlorocarbonate to give the corresponding N-carboisobutoxy compound, which is further demethylated as in Example 19 to yield N-carboisobutoxy-3-tert-butyl-4-hydroxy-β-phenethylamine, m.p. 77° C. This is subjected to reaction with epibromohydrin and with carbamoylpiperazine to give compound (27), m.p. 167° C.

When ethyl chlorocarbonate is used instead of isobutyl chlorocarbonate and the same reaction is carried out, 1-carbamyl-4-{3-[2-t-butyl-4-(2-carbethoxyaminoethyl)phenoxy]-2-hydroxypropyl}piperazine, compound (22), is obtained, m.p. 156° C.

EXAMPLE 22

Synthesis of compound (34) R=

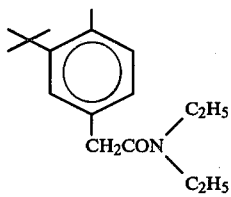

3-tert-Butyl-4-methoxybenzyl cyanide, obtained in Example 21, is hydrolyzed as in Example 20 to give 3-tert-butyl-4-methoxyphenylacetic acid. Melting point 93°–94° C. This is further treated as described in Example 20 to yield N,N-diethyl-3-tert-butyl-4-hydroxyphenylacetamide, m.p. 124°–126° C., which is allowed to react with epibromohydrin and then with carbamoylpiperazine similarly to give compound (34), melting point 138°–140° C.

When dibutylamine is used instead of diethylamine and the same reaction as above is carried out to give 1-carbamyl-4-[3-(2-t-butyl-4-N,N-diethylcarbamylmethylphenoxy)-2-hydroxypropyl]piperazine, compound (35), m.p. 108°–110° C.

EXAMPLE 23

Synthesis of compound (36) R=

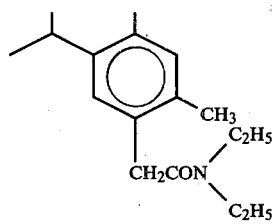

o-Methylthymol is allowed to react as in Example 19 to give 2-methyl-4-methoxy-5-isopropylbenzyl cyanide, b.p. 127°–130° C./0.9 mmHg. This is hydrolyzed as in Example 20 to yield 2-methyl-4-methoxy-5-isopropylphenylacetic acid, m.p. 107°–109° C., which is allowed to react as in Example 20 to yield N,N-diethyl-2-methyl-4-hydroxy-5-isopropylphenylacetamide, m.p. 138°–139° C. This is treated with epibromohydrin and then with carbamoylpiperazine to yield compound (36), m.p. 138°–141° C.

When dibutylamine is used instead of diethylamine in this reaction sequence, 1-carbamyl-4-[3-(2-isopropyl-4-N,N-dibutylcarbamylmethyl-5-methylphenoxy)-2-hydroxypropyl]piperazine, compound (21), m.p. 95°–97° C., is obtained.

EXAMPLE 24

Synthesis of compound (29) R=

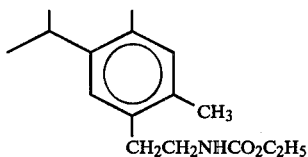

2-Methyl-4-methoxy-5-isopropylbenzylcyanide, obtained in Example 23, is reduced with aluminum hydride as in Example 19, then allowed to react with ethyl chlorocarbonate, and the resulting urethane compound is similarly subjected to dimethylation. The resulting N-carboethoxy-2-methyl-4-hydroxy-5-isopropyl-β-phenethylamine is allowed to react with epibromohydrin and then with carbamoylpiperazine to yield compound (29). The hydrochloride, recrystallized from isopropanol, melts at 135°–138° C.

When isobutyl chlorocarbonate is used instead of ethyl chlorocarbonate in this reaction, 1-carbamyl-4-{3-[2-isopropyl-4-(2-carboisobutoxyaminoethyl)-5-methylphenoxy]-2-hydroxypropyl}-piperazine, compound (30), melting point 92°–94° C., is obtained.

EXAMPLE 25

Synthesis of compound (23) R= o-Cyclohexylanisole is allowed to react by the same manner as in Example 19 to give 3-cyclohexyl-4- methoxybenzyl cyanide. This is purified by subjecting to silica gel column chromatography (solvent:benzene). This is hydrolyzed as in Example 20 to give 3-cyclohexyl-4-methoxyphenylacetic acid, m.p. 112°–114° C. This is then treated with n-butylamine as in Example 20 and then demethylated to give N-butyl-3-cyclohexyl-4-hydroxyphenylacetamide, m.p. 118°–120° C., which is allowed to react with epibromohydrin and then with carbamoylpiperazine to give compound (23), melting point 148°–149° C.

EXAMPLE 26

Synthesis of compound (28) R=

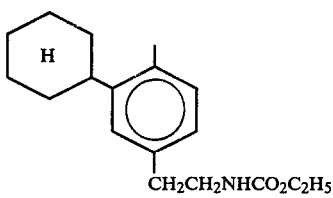

3-Cyclohexyl-4-methoxybenzylcyanide, obtained in Example 25, is reduced as in Example 19 and the resulting phenethylamine compound is allowed to react with ethyl chlorocarbonate to give the corresponding urethane compound. This is demethylated to give N-carboethoxy-3-cyclohexyl-4-hydroxy-β-phenethylamine, m.p. 97°–98° C., and allowed to react with epibromohydrin and then with carbamoylpiperazine by the same manner to give the compound (28), the hydrochloride of which melts at 101°–103° C.

EXAMPLE 27

Synthesis of compound (37) R=

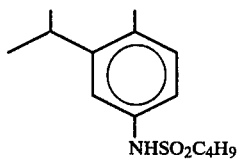

2-Isopropyl-4-nitrophenyl (18.1 g) is dissolved in 300 ml of methyl ethyl ketone, 22 g of anhydrous potassium carbonate and 68 g of epibromohydrin are added thereto, and the mixture is heated at reflux with stirring for three hours. The reaction solution is filtered to remove insoluble matter and the filtrate is concentrated in vacuo, and extracted with ether to give 20.1 g of 2-isopropyl-4-nitrophenyl glycidyl ether, m.p. 60°–62° C.

This glycidyl ether (4.7 g) and 4.7 g of carbamoylpiperazine are dissolved in 50 ml of methanol and the mixture is heated at reflux for five hours. The reaction solution is evaporated to dryness in vacuo, and the residual product is purified by silica gel column chromatography with 9:1 chloroform:methanol. Yield: 10.2 g.

This resulting product (3.3 g) is dissolved in 20 ml of ethanol, about 1 ml of Raney Nickel catalyst is added thereto, and the mixture is subjected to a catalyst reduction at room temperature under ordinary pressure. After absorption of hydrogen ceases, the catalyst is removed by filtration, the filtrate is evaporated to dryness in vacuo, and the residual product is purified silica gel column chromatography with 4:1 chloroform:methanol to give 2.1 g of the intermediate compound. Mass spectrum: M+ (m/e)=336. This compound (1.13 g) is dissolved in 6 ml of pyridine and 0.52 g of n-butanesulfonyl chloride is added dropwise with cooling (ice) and stirring. The mixture is stirred for two hours with cooling, diluted with 100 ml of ice water, and extracted with ethyl acetate. The resulting extract is subjected to purification by silica gel column chromatography with 4:1 chloroform:methanol to give 0.85 g of compound (37). The hydrochloride, recrystallized from ethanol, melts at 111°–113° C.

When propanesulfonyl chloride is used instead of n-butanesulfonyl chloride in this reaction, 1-carbamyl-4-[3-(2-isopropyl-4-n-propylsulfonamidophenoxy)-2-hydroxypropyl]piperazine, compound (24), is obtained. The hydrochloride, recrystallized from isopropanol, melts at 117°–119° C.

What is claimed is:

1. A compound of the formula:

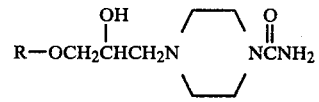

or a pharmaceutically acceptable salt thereof, wherein R is

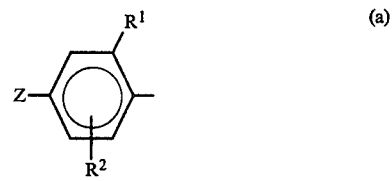 (a)

in which
 R¹ is alkyl of up to 6 carbon atoms, cycloalkyl of 3 to 7 carbon atoms or alkanoyl of up to 6 carbon atoms
 R² is hydrogen or alkyl of up to 6 carbon atoms, and
 Z is —CH₂CH₂NHCO₂R³, —NHSO₂R³ or

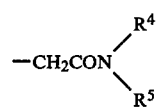

in which
 R³ is alkyl of up to 4 carbon atoms and each of R⁴ and R⁵ independently of the other is alkyl of up to 4 carbon atoms, or
(b) a bicyclic group of the formula:

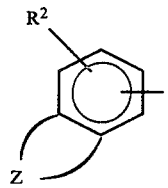

in which
 Z is a chain of 3 or 4 atoms, said chain being selected from the group consisting of —(CH₂)₂(CH₂)ₙ—; —CH=CH—(CH₂)ₙ—;

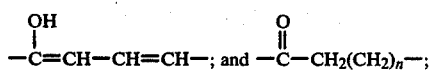

n has a value of 1 or 2 and $R^2$ is as herein defined.

2. A compound according to claim 1 wherein R is

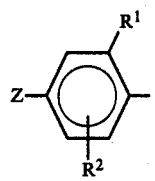

in which $R^1$ is alkyl of up to 6 carbon atoms, cycloalkyl of 3 to 7 carbon atoms or alkanoyl of up to 6 carbon atoms $R^2$ is hydrogen or alkyl of up to 6 carbon atoms, and Z is —$CH_2CH_2NHCO_2R^3$, —$NHSO_2R^3$ or

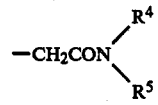

in which $R^3$ is alkyl of up to 4 carbon atoms and each of $R^4$ and $R^5$ independently of the other is alkyl of up to 4 carbon atoms.

3. A compound according to claim 1 wherein R is

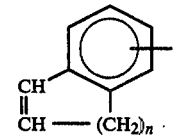

in which n has a value of 1 or 2.

4. A compound according to claim 1 wherein R is

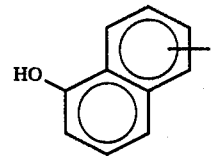

in which n has a value of 1 or 2.

5. A compound according to claim 1 wherein R is

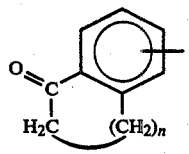

6. A compound according to claim 1 wherein R is

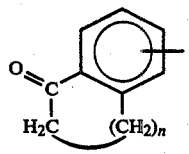

in which n has a value of 1 or 2.

7. The method of effecting β-adrenergic blocking activity in humans and other animals which comprises administering thereto an effective amount of a compound according to claim 1.

8. A pharmaceutical composition comprising an amount of a compound according to claim 1 sufficient to effect a β-adrenergic blocking response in combination with a pharmaceutically acceptable carrier.

* * * * *